United States Patent [19]

Nilsson

[11] Patent Number: 5,361,769
[45] Date of Patent: Nov. 8, 1994

[54] METHOD AND A SYSTEM FOR MEASURING FLUID FLOW MOVEMENTS BY A LASER-DOPPLER TECHNIQUE

[76] Inventor: Gert Nilsson, Lövsbergsvägen 13, 582 69 Linköping, Sweden

[21] Appl. No.: 39,410

[22] PCT Filed: Aug. 21, 1992

[86] PCT No.: PCT/SE92/00570
  § 371 Date: Apr. 21, 1993
  § 102(e) Date: Apr. 21, 1993

[87] PCT Pub. No.: WO93/03667
  PCT Pub. Date: Mar. 4, 1993

[30] Foreign Application Priority Data
  Aug. 22, 1991 [SE] Sweden .............. 9102421-6

[51] Int. Cl.$^5$ .............................. A61B 5/026
[52] U.S. Cl. .................... 128/666; 128/691; 356/28
[58] Field of Search .............. 128/664–667, 128/691; 356/28

[56] References Cited

U.S. PATENT DOCUMENTS 4,862,894  9/1989  Fuji ..................... 128/666

FOREIGN PATENT DOCUMENTS 0488614  6/1992  European Pat. Off. .
WO9011044  10/1990  WIPO .
WO9106244  6/1991  WIPO .

*Primary Examiner*—Ruth S. Smith
*Attorney, Agent, or Firm*—Browdy and Neimark

[57] ABSTRACT

The invention relates to a method and to a system for reducing the distance-dependent amplification factor when measuring fluid flow movements with the aid of an image-producing laser-Doppler technique, in particular when measuring blood perfusion through tissue. A laser beam source (1) directs a laser beam (2) onto a measurement object (5), which scatters and reflects the beam (2). The reflected light is received by a detector (9) which senses the broadening in frequency caused by the Doppler effect. One or more lenses (12: 15, 16) are placed in the path of the beam (2) and are intended to maintain constant the number of coherence areas on the detecting surface of the detector and independent of the distance between detector and measurement object.

13 Claims, 5 Drawing Sheets

METHOD AND A SYSTEM FOR MEASURING FLUID FLOW MOVEMENTS BY A LASER-DOPPLER TECHNIQUE

FIELD OF INVENTION

The present invention relates to a method and to a system for reducing the distance-dependent amplification factor when measuring fluid flow movements with an image-producing laser-Doppler technique, particularly when measuring blood perfusion through tissue. The system includes a laser beam generating source and means for directing the laser beam onto a measurement object which scatters and reflects the light beam. The light reflected is received by a detector which detects broadening of the frequency caused by the Doppler effect.

BACKGROUND OF THE INVENTION

The invention is based on the use of the known laser-Doppler technique for measuring the superficial circulation of blood in cutaneous tissue. This technique is described, for instance, in U.S. Pat. Nos. 3,511,227, 4,109,647, SE 419 678 and tile articles "In Vivo Evaluation of Microcirculation by Coherent Light Scattering", Stern, N. D., Nature, Vol. 254, pp. 56–58, 1975; "A New Instrument for Continuous Measurement of Tissue Blood Flow by Light Beating Spectroscopy", Nilsson, G. E., Tenland, T. and Öberg, P. A., IEE trans., BME-27, pp. 12–19, 1980, and "Evaluation of a Laser Doppler Flow Meter for Measurement of Tissue Blood Flow", Nilsson, G. E., Tenland, T. and Öberg, P. A., IEE trans., BME-27, pp. 597–604, 1980. In principle, this technique involves directing a laser beam onto a part of the tissue and receiving, with the aid of an appropriate photodetector, part of the light scattered and reflected back by that part of the tissue that is irradiated by the laser beam. As a result of the Doppler effect, the frequency of the reflected and scattered light is broadened and the frequency spectrum of the light will thus be broader than the frequency spectrum of the original laser beam, this broadening of the light frequency being due to the influence of movement of blood cells in the superficial part of the irradiated tissue. The extent to which the frequency is broadened and the intensity of light within different parts of this broader frequency spectrum constitute a measurement of the superficial blood circulation in the irradiated part of the examined tissue and can be determined or evaluated by appropriate processing of the photodetector output signal.

Swedish Patent Application No. 8903641-2 describes how this technique is used in a system for measuring and visually presenting the extent of superficial blood circulation over a large area of a part of the body, for instance a complete hand or foot or a part of a hand or foot or a part of a leg. The superficial blood circulation can vary quite considerably within different regions of a body part, and the described system enables the course taken by an illness, disease or healing process to be studied effectively. This known system includes a laser light source for generating a laser beam and means for directing the laser beam onto the body part to be examined and for guided movement of the laser beam over said body part in accordance with a predetermined scanning pattern. The system also includes means for receiving light reflected from said body part and for detecting the broadening in frequency of the reflected light caused by the Doppler effect, and also for registering this broadening of the frequency over a large number of points along the path scanned by the laser as a measurement of the superficial blood circulation in said body part at said points. The system also includes means for visual presentation on a color screen of the magnitude of the superficial blood circulation at the scanned points, using mutually different colors for mutually different blood circulation magnitude intervals.

When practicing the light-fiber-based Doppler effect described in the introduction, registration of the superficial blood circulation is effected solely with the aid of a punctiform measuring process. In the technique described in Swedish Patent Application No. 8903641-2, the laser beam scans different measuring points over a wide surface area, so as finally to generate an image or picture of the microcirculation of the surface scanned. In order to be able to compare mutually all of the measurement values registered at the various measurement points over this area, it is necessary for the different conditions that prevail during the measuring procedure to be equal when taking the comparison measurements. This is often not the case with regard to the position of the detector in relation to the measurement points on the measured object, which leads to uncertainty when making a comparison study between the values measured on different occasions. In the case of the image-producing system in which the laser beam scans the measurement object, the distance between the measurement object point and the detector surface, and therewith also the angle of the reflected beam in relation to the detector, will vary during scanning of the body part. Consequently, the system amplification factor for the measured signal will vary within one and the same image, or picture, which introduces a distortion in the reproduction of the blood flow image.

The theory of how such distance-dependent-amplification occurs is described comprehensively in Swedish Patent Application No. 9002467-0. It is described in this application that, in addition to the angle $\alpha$ between the normal of the detector surface and the line from which the light spot on the object is seen from the detector, the distance-dependent-amplification is mainly due to the fact that the size of the coherence area ($A_{coh}$) on the detector surface is a function of the solid angle ($\Omega$) at which the light spot on the object is seen from the detector, in accordance with the formula:

$$A_{coh} = \lambda^2/\Omega \qquad (1)$$

The solid angle $\Omega$ a is dependent on the distance X between the detector and the measurement object, the diameter of the light spot on the object ($d_s$) and the wave length $\lambda$ according to the equation $$A_{coh} = (4\lambda X/d_s)^2 \qquad (2)$$

Described in Swedish Patent Application No. 9002467-0 is a method for compensating this distance-dependent coherence-area size and therewith system amplification. In this application, the number of coherence areas N and therewith the amplification is described as a function of the distance X between measurement object and detector, in accordance with the equation $$N = \pi(r_d r_s/2\lambda X)^2 \cos \alpha \qquad (3)$$

where $r_d$=detector radius,
$r_s$=laser beam radius.

When the beam is located immediately beneath the detector, the number of coherence areas will be $$N=\pi(r_d r_s/2\lambda D)^2$$

where D is the perpendicular distance between detector plane and measurement object.

According to the application, this distance D can be measured by registering the time taken for an ultrasonic pulse to travel to the measurement object from an ultrasonic detector placed on a level with the light detector, and reflected back to the ultrasonic detector. The distance X can be calculated on the basis of this time lapse and the atmospheric speed of sound. Since D is constant and known, the size $A_{coh}$ of the coherence area can also be calculated. When the angle $\alpha$ between the normal of the detector surface and the direction from which the light spot is seen on the object from the photodetector, it is possible to calculate and compensate for the total number of coherence areas on the detected surface, and therewith also the amplification factor. When carrying out the method in practice, the distance X is calculated for each measurement point, by measuring the perpendicular distance between the detector surface and the measurement object prior to starting collection of the images, and the distance between the measurement object point immediately beneath the detector and the measuring point concerned is calculated, for instance, by detecting the positions of the scanner mirrors.

This method has been found to produce good results with measurement objects which are relatively flat. However, when the scanned surface is irregular, such as the upper skin of a hand, the value of the distance X obtained with this method will deviate from the true value, and there is also a risk that the ultrasonic pulse will be reflected away and not registered by the ultrasonic receiver. Thus, the measuring accuracy of the construction described in Swedish Application No. 9002467-0 is limited in those cases when the measurement object has an irregular or uneven measurement surface.

The Basic Concept of the Invention

The object of the present invention is to solve the aforesaid problems with the aid of a method and a system which are devised so that the amplification factor, and therewith the number of coherence areas on the detector surface, will be kept constant and independent of the distance between detector and measurement object and also independent of the angle $\alpha$ between the normal of the detector surface and the line along which the light spot is seen from the detector. This will result in correct presentation of the measured flow values, even when the surfaces of the measurement object are rough and irregular. According to the present invention, this is achieved with a method and a system set forth in the following claims.

Variations in the angle $\alpha$ can be readily compensated for, by measuring the angle continuously and registering the measurements obtained with a starting point from the position of those drive means which control the scanner mirrors, and therewith the position of the light spot. In this case, the angle compensation factor is proportional to cos $\alpha$.

The invention is based on the concept of a method and a system which will render the size of the coherence area $A_{coh}$ independent of the distance between detector and measurement object. According to the present invention, this is achieved by maintaining the number of coherence areas on the detecting detector surface constant. According to one preferred embodiment of the invention, this can be achieved by causing the laser beams to diverge so that the diameter of the light spot on the measurement object will be proportional to the distance X between the detector and the measurement object at each measurement point.

BRIEF DESCRIPTION OF THE ACCOMPANYING DRAWINGS

The invention will now be described in more detail with reference to the accompanying drawings, in which FIG. 1 illustrates schematically, and by way of example, an arrangement for measuring and visually presenting the blood flow in a hand;

DETAILED DESCRIPTION OF THE INVENTION

Figure 1:
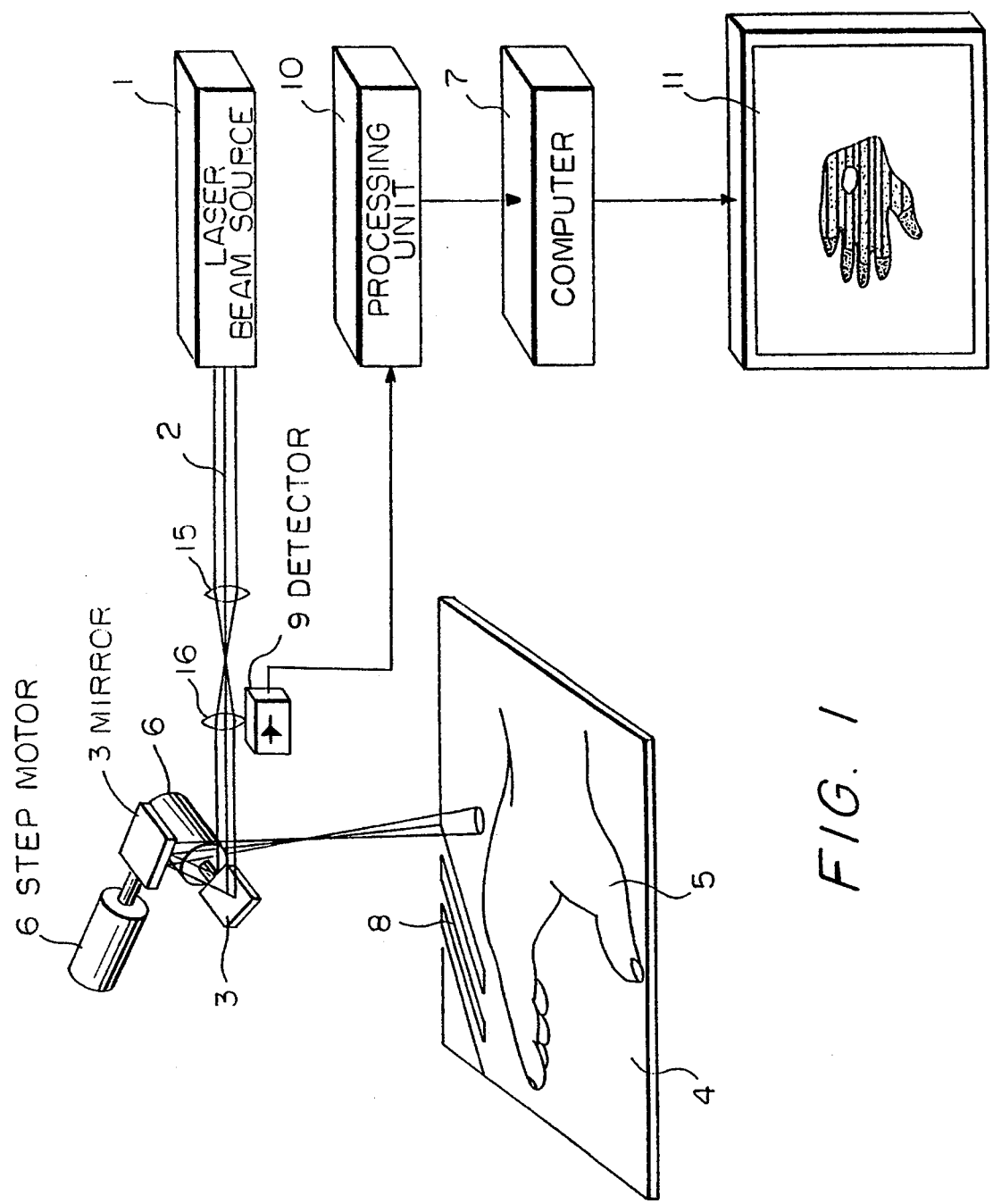

FIG. 1 illustrates schematically a system for the measurement and visual presentation of the superficial blood flow in a hand, and comprises a conventional laser beam generating source 1 which produces a laser beam 2. The laser beam is directed onto an underlay 4, which supports the part of the body to be examined, with the aid of suitable optical elements, of which two mirrors 3 are shown in FIG. 1. The two mirrors can be swung by means of stepping motors 6 controlled by a computer 7, also illustrated schematically.

The laser beam is caused to scan the body part 5 in accordance with a predetermined scanning pattern 8. Scanning movement of the laser beam 2 is preferably carried out in stages, or stepwise, so as to obtain a plurality of scanning points or measuring points located sequentially along the scanning path.

When the beam 2 impinges on the body part 5, the beam will be scattered and reflected in the superficial tissue, and therewith also partially by the blood cells in the superficial blood circulation in the measuring point concerned on the body part. Part of this scattered and reflected light is captured, e.g., by a suitable photodetector 9 whose output signal is delivered to a signal processing unit 10. The frequency of the light received by the photodetector 9 is broader than the frequency of the light in the original laser beam 2, which with regard to its size and the light intensity in different parts of the frequency spectrum constitutes a measurement of the magnitude of the superficial blood circulation at the measurement point concerned. A measurement of the size of the superficial blood circulation can be determined for each measurement point on the body part 5 examined, by appropriate processing of the photodetector output signal in the signal processing unit 10. These measurement values are delivered to the computer 7 and stored therein for all measurement points along the scanning path 8 of the laser beam 2. A visual presentation or picture of the examined body part 5 can be produced with the aid of a color monitor 11 connected to the computer, wherein each measurement point, i.e. each picture pixel, is given a specific color corresponding to the size range within which the superficial blood circulation in corresponding measurement points on the body part lie.

Figure 2:
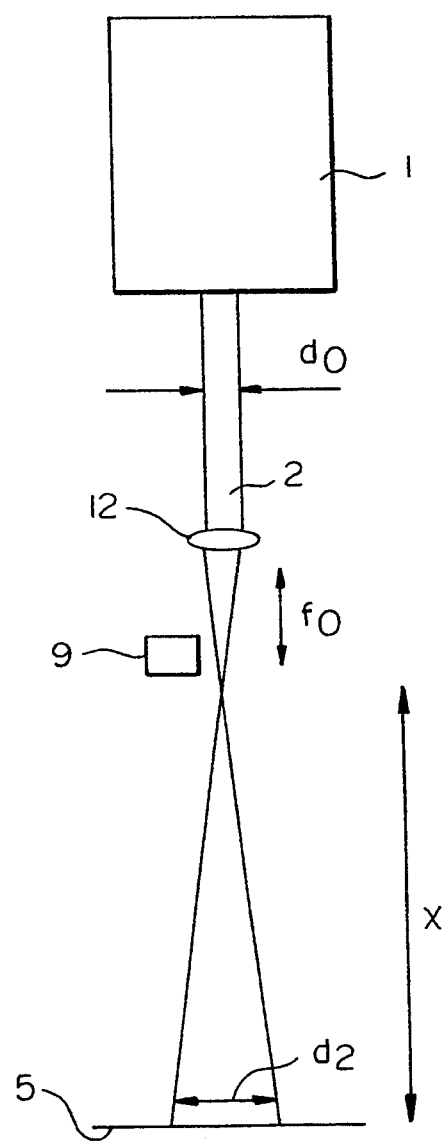
FIG. 2 illustrates schematically a first embodiment of the invention.

FIG. 2 is a simplified illustration of the principles of the present invention, with certain of the components shown in FIG. 1 omitted for the sake of clarity. Illustrated schematically in FIG. 2 is a laser beam source 1, which emits a laser beam 2 having an initial width $d_0$, the detector 9 and the measurement object 5. The Figure illustrates schematically how the width of the laser beam on the measurement object $d_2$ is made dependent on and directly proportional to the distance X between the detector and the measurement object. This is achieved by placing a lens 12 of focal length $f_0$ at a distance from the detector 9. The lens is constructed and arranged so that the focal point of the beam will lie in the detector plane, wherein broadening $d_2$ of the beam on the measurement object will be directly proportional to the distance X between detector and object. In the above equation (3) the quotient $r_s/X$ will thus in this case assume a constant value, which means that the number of coherence areas on the detector surface, and therewith the amplification factor, will also be constant.

Figure 3:
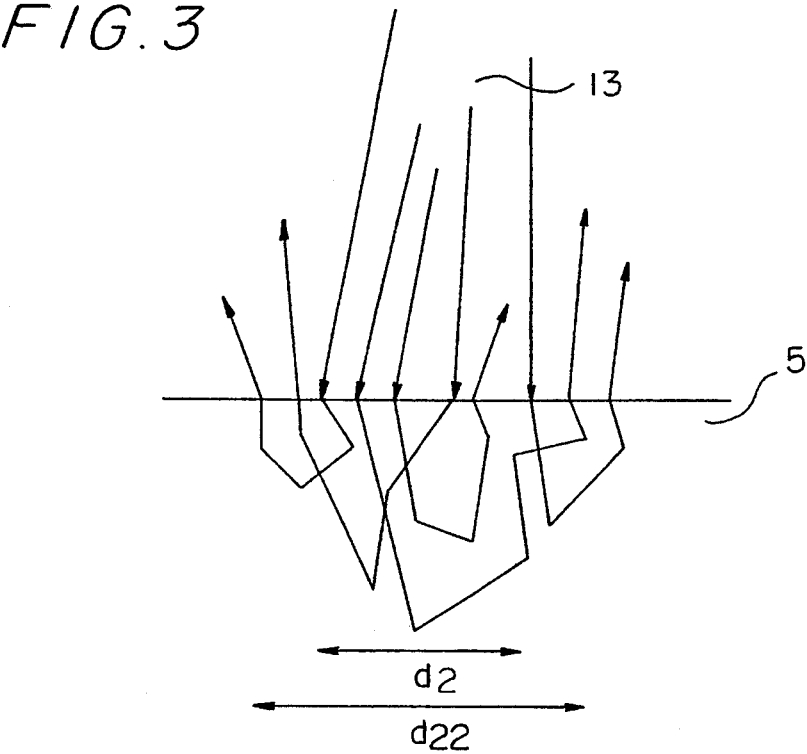
FIG. 3 illustrates schematically propagation of the light spot on the measurement object.

Broadening of the light spot on the measurement object, however, will, in addition to the width of the beam in air, also depend on the diffusion broadening which occurs as a result of the photons penetrating to a certain depth in the measurement object prior to returning to the object surface. This course of events is illustrated in FIG. 3. Consequently, the actual size of the light spot on the measurement object will depend on diffusion broadening in addition to depending on the distance between the focal point of the lens and the object and the focal length of said lens. This diffusion broadening is independent of the distance between measurement object and detector. FIG. 3 shows that the beam 13 incident on the measurement object, said beam having a width $d_2$ in air, forms on the measurement object a light spot of width $d_{22}$, in that some photons will diffuse through the tissue and exit from the tissue sideways and thus outside the surface of the incident beam.

Figure 4:
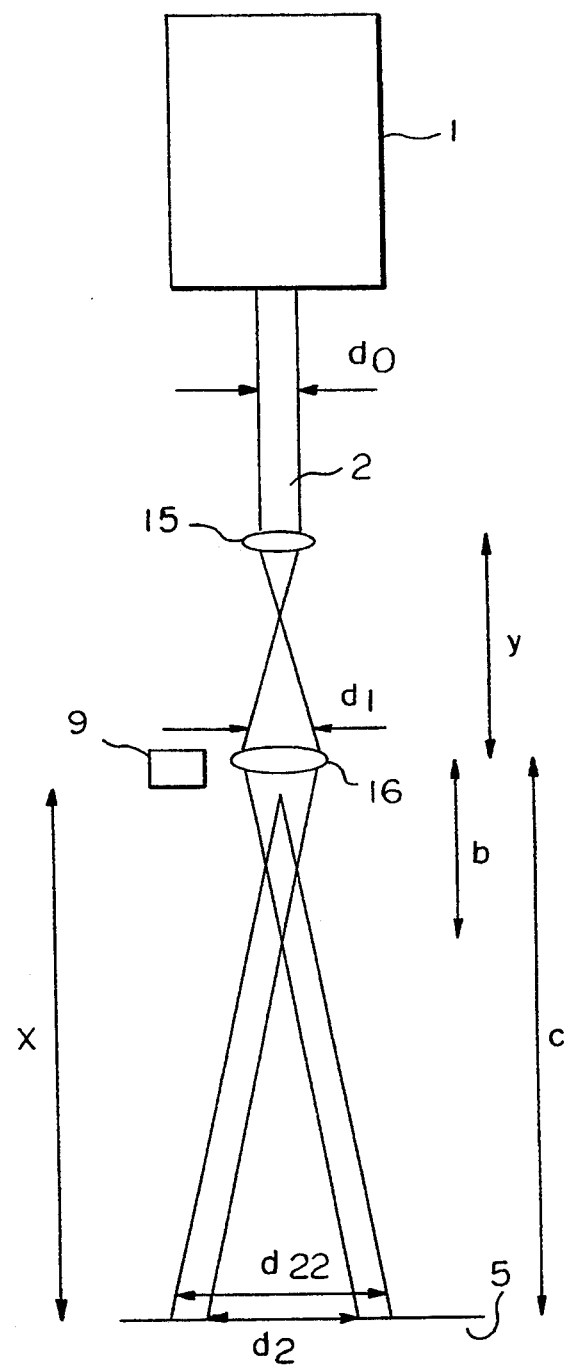
FIG. 4 illustrates schematically a second embodiment of the invention.

FIG. 4 illustrates schematically an inventive embodiment which takes into account the effects of the aforedescribed diffusion broadening, certain components being excluded in the FIG. 4 illustration for the sake of clarity. In the case of this solution, a first lens 15 having a focal length $f_0$ and a second lens 16 having a focal length $f_1$ have been placed in the beam path. This introduction of a further lens causes the focal point of the system to lie at a certain distance from the detector while, at the same time, obtaining a predetermined beam width on the measurement object. The use of said two lenses affords the possibility of diverging the beam and also of determining the position of the focal point and the width of the beam at a given distance from the focal point, in accordance with the following relationships:

$$d_0/d_1 = f_0/(Y-f_0);$$

$$d_1/d_2 = b/(c-b);$$

$$1/f_1 = 1/(y-f_0) + 1/b;$$

$$X/(c-b) = d_{22}/d_2$$

where
$d_0$ = the original width of the laser beam
$f_0$ = the focal length of the upper lens
$d_1$ = the width of the beam at the lower lens
$f_1$ = the focal length of the lower lens
y = the distance between the lenses
b = the distance between the lower lens and the focal point of the system
c = the distance from the lower lens to the object
$d_2$ = the width of the beam in air at the object
$d_{22}$ = the width of the light spot on the object
X = the distance between the detector and the measurement object These relationships, and FIG. 4, show how the parameters shall be selected in order for the size of the light spot on the object to be proportional to the distance between the detector surface and the measurement object. In an optimal setting, the quotient $d_{22}/X$ will therewith be constant, which means that the number of coherence areas on the detector surface, and therewith the amplification factor, will also be constant and independent of the distance between detector and measurement object.

A typical value of $d_2$ in practice is about 2 mm, while a typical value of $d_0$ is about 0.8 mm. Thus, when practicing the inventive method, changes in the amplification factor can be limited to about +/−6%, as distinct to the earlier case of about +/−70%, within a distance between detector and measurement object of 11-22 cm.

Figure 5:
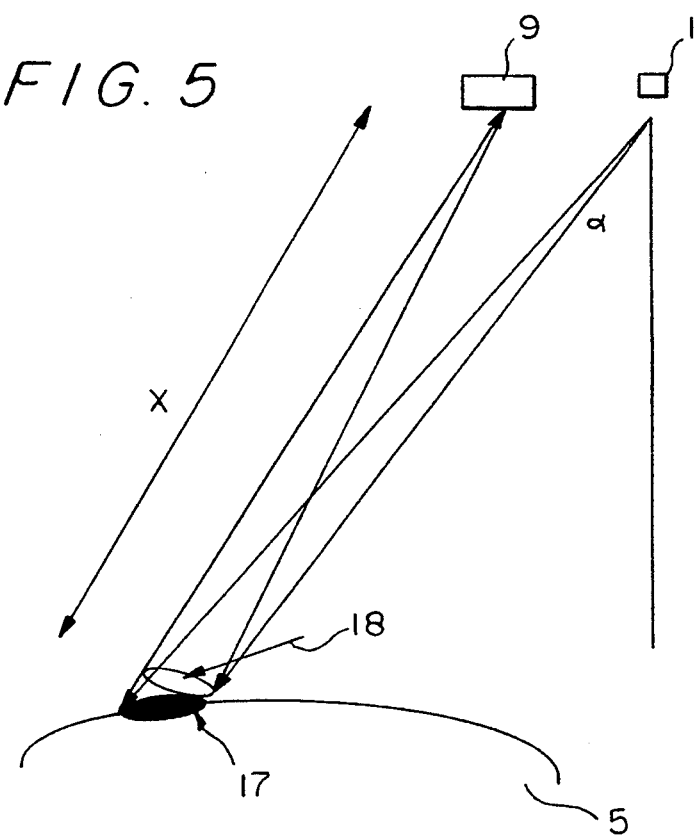
FIG. 5 illustrates the extension of the light spot on the measurement object as the spot is seen from the detector.

FIG. 5 illustrates schematically the extension of the light spot on the object as seen from the detector, when the light beam is not placed along the normal of the photodetector surface immediately beneath the detector. As shown in the Figure, the surface of the light spot on the measurement object will have an elliptical form 17 in this case. The light spot surface seen by the photodetector, however, will still be circular, 18, in principle, as evident from FIG. 5. This means, in turn, that the number of coherence areas on the detector surface will be independent of the distance between detector and measurement object point, subsequent to compensating for the angle α.

Similarly, the actual light spot on a non-planar measurement object surface will be seen from the photodetector as a circular surface. This enables amplification compensation to be made also for non-planar measurement objects.

Figure 6:
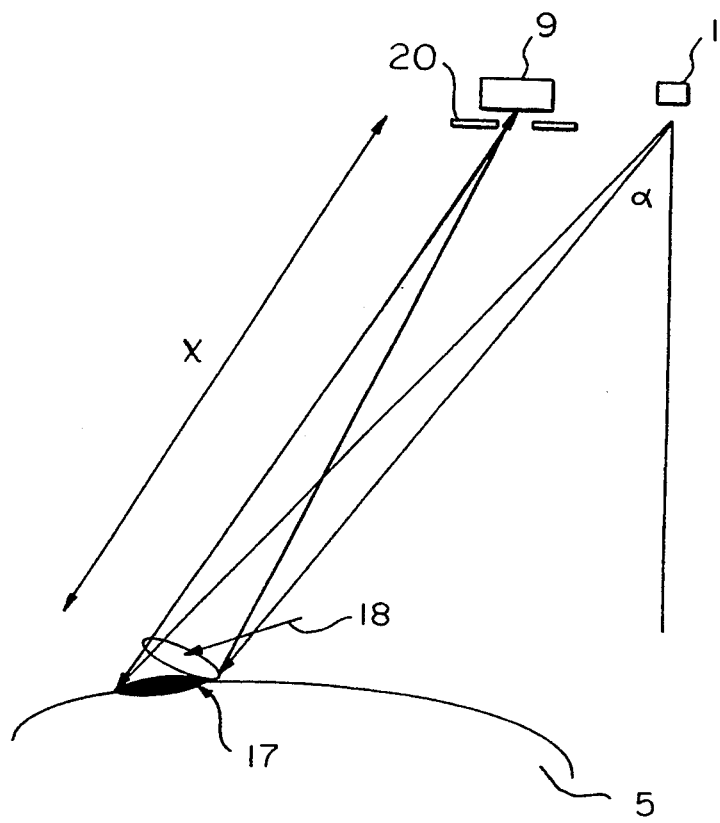
FIG. 6 illustrates shutter means to shutter the detecting surface.

It will be understood that the invention is not limited to the aforedescribed exemplifying embodiments thereof, and that several modifications are conceivable within the scope of the following claims. For example, although the illustrated embodiments include a lens system that includes one or two lenses positioned in the beam path, it will be understood that a system that includes more than two lenses is also included within the concept of the present invention. Furthermore, the illustrated lens system shown by way of example can be replaced with shutter means in the form of diaphragm 20 shown in FIG. 6. for successively shuttering the detector surface, so that the active detector surface will decrease when the measurement object lies closer to the detector and the coherence area will have a smaller extension. This will result in a constant value of the number of coherence areas on the active detector surface and therewith in an amplification factor which is independent of the distance between detector and measurement object.

I claim:

1. A method for measuring fluid flow movements, said method comprising the steps of:
   directing a laser beam (2) generated by a laser beam source (1) onto a measurement object (5) which scatters and reflects the laser beam (2);
   receiving and detecting scattered and reflected light from said measurement object (5) in a detector (9) and detecting a broadening in frequency caused by a Doppler effect;
   maintaining a number of coherence areas on a detector surface of said detector (9) constant and independent of a distance between said detector (9) and said measurement object (5).

2. A method according to claim 1, wherein the number of coherence areas on the detector surface of said detector (9) is kept constant by causing the laser beam (2) to diverge in a direction towards the measurement object.

3. A method according to claim 2, further comprising the steps of:
   moving the laser beam (2) over the measurement object (5) in a specific scanning pattern, such that the detector (9) will receive and detect the light reflected from a large number of measurement points (M) along the scanning path; and in each of these measurement points (M) registering and compensating for an angle $\alpha$ between a normal of the detector surface and a line from which the measurement point (M) on the measurement object (5) is seen from the detector (9).

4. A method according to claim 2, wherein divergence of the light beam (2) is achieved by refraction of the beam through a lens (12) whose focal point coincides with the detector surface plane.

5. A method according to claim 4, further comprising the steps of:
   moving the laser beam (2) over the measurement object (5) in a specific scanning pattern, such that the detector (9) will receive and detect the light reflected from a large number of measurement points (M) along the scanning path; and in each of these measurement points (M) registering and compensating for an angle $\alpha$ between a normal of the detector surface and a line from which the measurement point (M) on the measurement object (5) is seen from the detector (9).

6. A method according to claim 2, wherein divergence of the laser beam (2) is achieved, by refraction of the beam through a plurality of lenses (15, 16) placed at a given distance from one another.

7. A method according to claim 6, further comprising the steps of:
   moving the laser beam (2) over the measurement object (5) in a specific scanning pattern, such that the detector (9) will receive and detect the light reflected from a large number of measurement points (M) along the scanning path; and in each of these measurement points (M) registering and compensating for an angle $\alpha$ between a normal of the detector surface and a line from which the measurement point (M) on the measurement object (5) is seen from the detector (9).

8. A method according to claim 1, further comprising the steps of:
   moving the laser beam (2) over the measurement object (5) in a specific scanning pattern, such that the detector (9) will receive and detect the light reflected from a large number of measurement points (M) along the scanning path; and, in each of these measurement points (M), registering and compensating for an angle $\alpha$ between a normal of the detector surface and a line from which the measurement point (M) on the measurement object (5) is seen from the detector (9).

9. A system for measuring fluid flow movements, said system comprising:
   a laser beam source (1) for generating a laser beam (2),
   means (3, 6) for directing the beam onto a measurement object (5) to be examined,
   detector means (9) located above the measurement object for receiving light reflected from the measurement object (5) and for detecting a broadening in frequency caused by a Doppler effect, and
   means (12; 15; 16; 20) for maintaining a constant number of coherence areas on a detecting surface of said detector means.

10. A system according to claim 9, wherein said means for maintaining includes a lens (12) through which said laser beam (2) is caused to pass and refract so as to diverge said beam in a direction towards said measurement object.

11. A system according to claim 10, wherein a focal point of said lens (12) coincides with the detector surface plane.

12. A system according to claim 9, wherein said means for maintaining includes two lenses (15, 16) placed at a given distance from one another and so that the laser beam is caused to pass through said lenses (15, 16) and is refracted so as to diverge said beam (2) in a direction towards said measurement object (5).

13. A system according to claim 9, wherein said means for maintaining includes a shutter means placed at the detector surface and intended to adjustably shutter the detector surface of the detector means (9) contingent on a distance between the detector and the measurement object such as to maintain the number of coherence areas on the detector surface constant.

* * * * *